United States Patent [19]

Pecheux

[11] Patent Number: 4,501,267
[45] Date of Patent: Feb. 26, 1985

[54] TRACTION-SUSPENSION DEVICE WITH TRANSOSSEOUS PIN

[75] Inventor: Jean-Claude Pecheux, Charleville-Mezieres, France

[73] Assignee: Societe Anonyme: Compagnie Generale de Materiel Orthopedique, Charleville-Mezieres, France

[21] Appl. No.: 438,929

[22] Filed: Nov. 3, 1982

[30] Foreign Application Priority Data

Nov. 5, 1981 [FR] France ............................. 81 20897

[51] Int. Cl.³ ............................................. A61F 5/04
[52] U.S. Cl. ............................... 128/84 R; 128/84 B; 128/85; 128/92 A
[58] Field of Search ................ 128/84 R, 84 A, 84 B, 128/84 C, 85, 92 A, 92 R, 92 B

[56] References Cited

U.S. PATENT DOCUMENTS 2,101,889  12/1937  Anderson ........................ 128/84 R
2,266,628  12/1941  Finochietto .................... 128/84 R

FOREIGN PATENT DOCUMENTS

| 641430 | 4/1964 | Belgium | 128/84 R |
| 671580 | 2/1939 | Fed. Rep. of Germany | 128/84 B |
| 824376 | 12/1951 | Fed. Rep. of Germany | 128/84 B |
| 869387 | 3/1953 | Fed. Rep. of Germany | 128/84 R |
| 718055 | 10/1931 | France | 128/92 A |
| 2295726 | 7/1976 | France | 128/84 R |

Primary Examiner—Ronald L. Frinks
Attorney, Agent, or Firm—Bacon & Thomas

[57] ABSTRACT

A traction-suspension device with transosseous pin having:

a tensioning pin and tension sleeves immobilizable in adjustable axial position on the pin, two support bearings receiving the sleeves via ball bearings, a traction-suspension hoop adaptable on the bearings, a tensioning stirrup adaptable between the bearings on assembling endpieces formed by the sleeves in facing relation.

The invention finds application with suspended-type splints.

8 Claims, 4 Drawing Figures

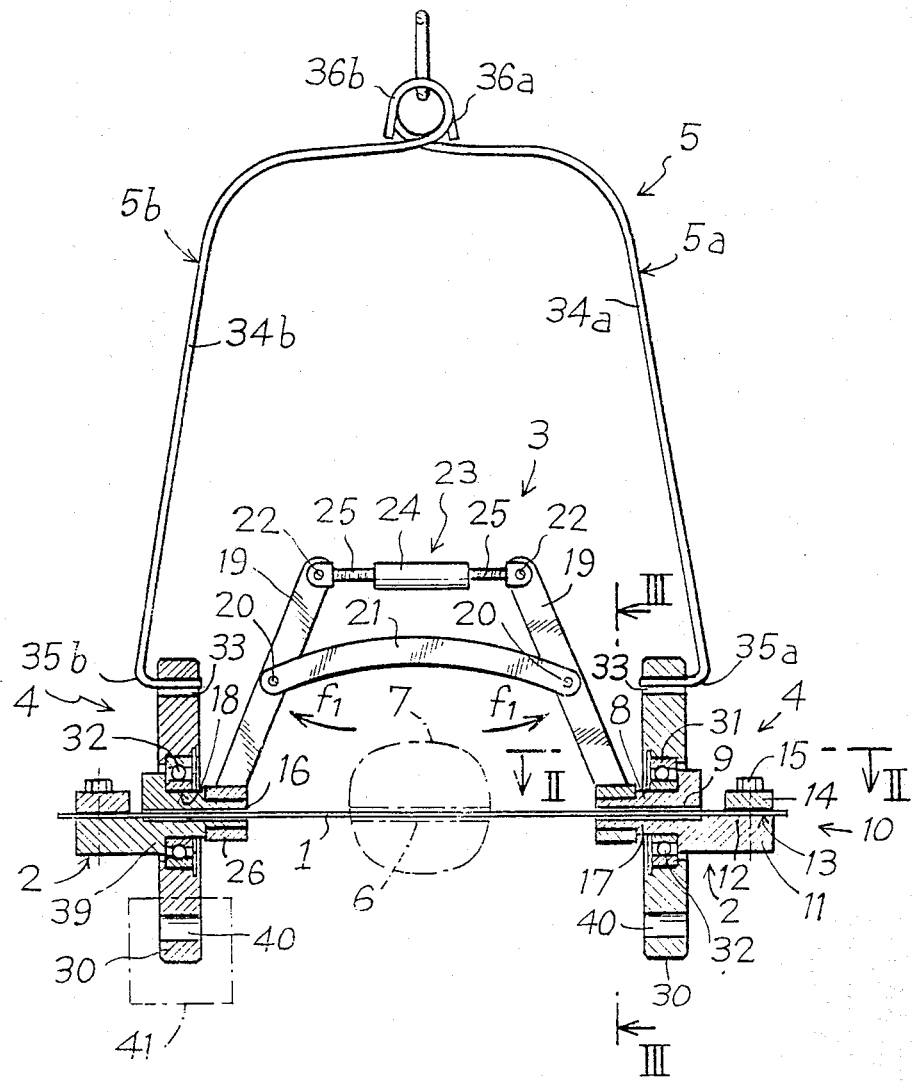

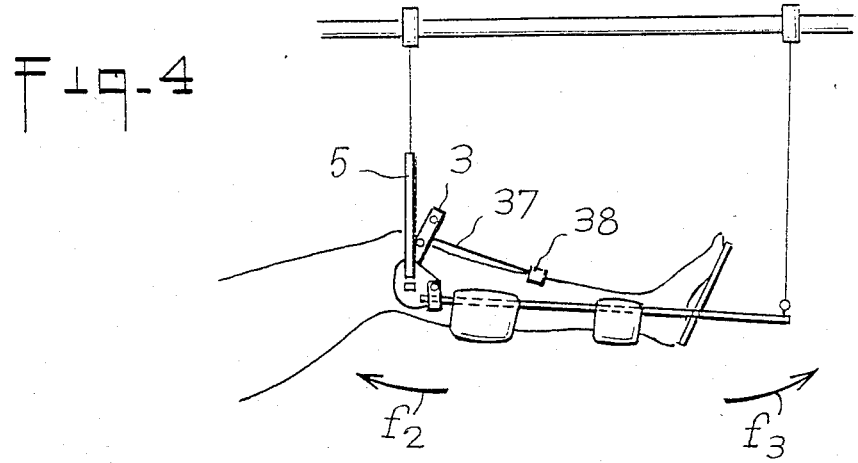
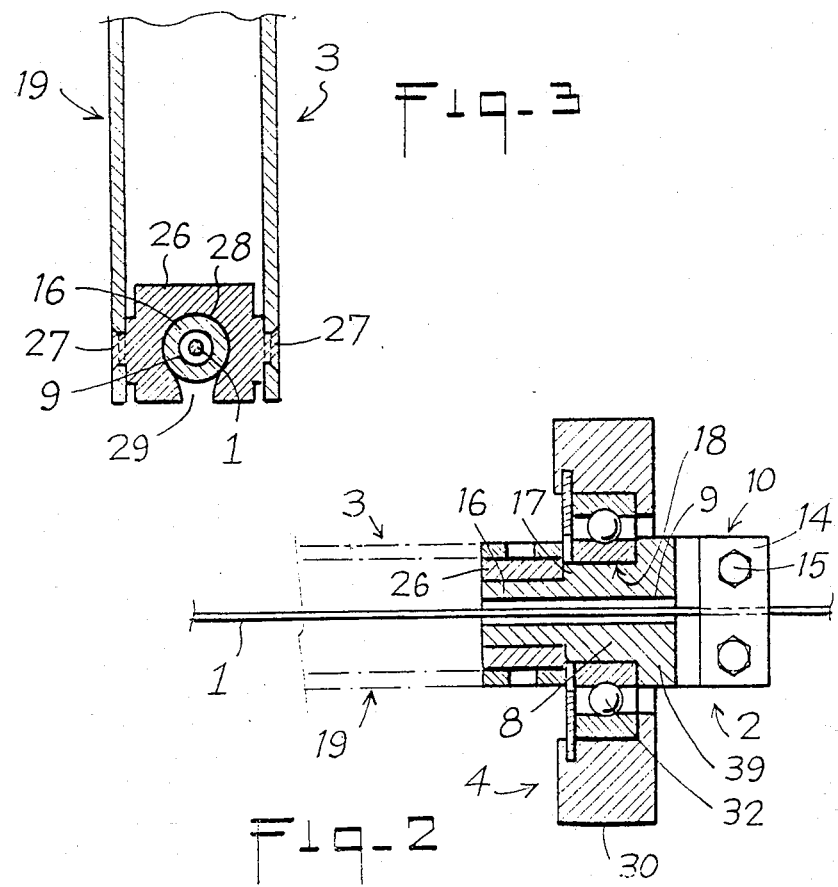

TRACTION-SUSPENSION DEVICE WITH TRANSOSSEOUS PIN

The present invention relates to the equipment used for orthopaedic treatment and functional reeducation of traumatized limbs, and more particularly to devices permitting, by way of a metallic pin going through the bone of the limb to be straightened or of the articulation to be supported, the application of a traction or suspension force to said limb or articulation.

A number of devices have already been proposed to this end. These devices can generically be called traction stirrups.

The first designs were composed of two arms articulated on a central member or yoke, through which is threaded a screw the end of which between the said arms is connected to the latter by way of two small rods, the other end being equipped with a control bar provided with at least one hole for hooking in a traction or suspension cable. The end portions of the arms of the stirrups are equipped with means connecting them with a pin, or metal rod, which is caused to go through the limb and its bone, so as to leave on either side of said limb, two end portions for adapting the arms of the stirrup.

After positioning, the screw is operated to cause the relative opening of the arms, thus creating a traction on the pin. The traction or suspension of the traumatized limb can thus be achieved from the stirrup.

Such a device is not really satisfactory whenever it is required to obtain, simultaneously to the traction or traction-suspension, a mobilization of the limb. Indeed, during the variation of the angulation between the articulations of a limb, there occurs a spatial displacement, with respect to a fixed point of the traction or traction-suspension cable connecting the stirrup. Said latter is as a result moved along an arc of circle inside the plane of the mobilization movement, so that the pin is made to turn inside the bone. Considering that the pin is, in actual fact, a steel rod of small cross-section, the tension applied thereto by the stirrup is not sufficient to make it absolutely rigid, and in addition to the rotation of the pin inside the bone, the pin can then be made to curve inside the limb.

The result is painful for the patient, with in some case an inflammation and a risk of infection.

In an attempt to solve this problem, the connecting means between the arms of the stirrup and the pin have been replaced by clamping jaws associated to ball bearings interposed between said jaws and the arms of the stirrup.

The experiments conducted with this type of equipment have shown that the aforementioned problem was still there. Indeed, the traction applied by the arms of the stirrup imposes an axial strain on the ball-bearings which cannot be designed or dimensioned to withstand such a strain. The free rotation which was the initial aim is as a result perturbed or braked, if not prevented.

Moreover, the radial strain which has to be born by the ball-bearings and which results from the suspension of a limb by way of the stirrup, is added to the axial strain and imposes on the ball-bearing an overall pressure which opposes the free rotation.

The tests carried out have shown that this type of equipment gives rise to the same painful reactions, since the pin is always driven into induced rotation inside the limb immediately the said limb is mobilized.

Another different solution has been proposed, still to the same end. According to said solution, the stirrup acts by the free end portions of its open arms on the longitudinal members of a deformable frame. Said longitudinal members are provided with holes for fitting in the ends of the traction pin by means of shrink rings with ball bearings resting against the longitudinal members.

Such a construction is no longer satisfactory because to apply a traction on the pin, it is necessary to act via the stirrup wide apart from the longitudinal members of the frame. This results in an axial strain being imposed on the ball bearings connecting the longitudinal members and the tension pin. The operation of these ball bearings is, as a result, hampered in the same way as with the preceding solutions.

In addition, the radial strains which are applied to the stirrup are also transmitted to the longitudinal members of the frame, and of course, they are also applied to the connecting bearings between the pin and the longitudinal members.

It is the object of the present invention to overcome the aforesaid problems encountered with the present devices and in particular to prevent the induced rotation of the traction pin inside the bone and inside the limb in the case of mobilization of a suspended limb or of a limb in suspension-traction.

One object of the invention is to propose an equipment capable of tensioning the transosseous pin, whilst immobilizing it with respect to its supporting structure and to the means used for the suspension and/or traction from said structure.

Another object of the invention is to propose an equipment which is strong but simple, and easily adaptable without any risk of a false maneuvering by the nursing staff.

Another object of the invention is to propose an equipment which eliminates all risks of incorrect assembly, and thus ensures the expected result.

Yet another object of the invention is to propose a device which is indifferently adaptable to suspension and/or traction means or to support means such as splints.

These objects are reached according to the present invention with a device comprising:
- a tensioning pin and tension sleeves immobilizable in adjustable axial position on the pin,
- two support bearings receiving the said sleeves via ball bearings,
- a traction-suspension hoop adaptable on the bearings,
- a tensioning stirrup adaptable between the bearings on assembling endpieces formed by the sleeves in facing relation.

The invention will be more readily understood on reading the following description with reference to the accompanying drawings in which:

FIG. 1 is a partial cross-section of an elevational view of the device according to the invention.

FIGS. 2 and 3 are respective cross-sections on a large scale, along lines II—II and III—III of FIG. 1.

FIG. 4 is a diagrammatical side view illustrating how the device according to the invention is used.

Referring now to the drawings, FIG. 1 shows that the device according to the invention comprises a pin 1 which is joined via two connecting sleeves 2, on the one hand, to a tension stirrup 3, and on the other hand, to two bearings 4 adaptable to a supporting structure which, in the illustrated example, is constituted by a suspension hoop 5.

The pin 1 is of a conventional type, meaning that it is formed by a metallic rod of diameter varying between 1 and 2 mm. Said rod can comprise, in its middle part, a helical standing-out portion 6, designed so as to allow a closer bond with the bone 7 of the limb which it is meant to go through.

Each sleeve 2 (FIGS. 1 and 2) comprises a core piece 8, provided axially with a bore 9 of diameter greater than that of the pin 1. Said bore 9 issues between the jaws of a clamp 10 which is formed at one end of the core piece 8. To this effect, the core piece 8 comprises an extension 11 which constitutes a fixed jaw with a bearing surface 12 on the level of which opens the bore 9. Preferably, the surface 12 is provided with a groove 13 of radius substantially equal to the radius of the pin 1. Said groove 13 extends in line with the orifice of the bore 9 with which it is co-axial. The bearing face 12 of the fixed jaw 11 is designed to support a movable jaw 14 which is in the form of a flange secured by way of two screws 15 on the face 12. Said movable jaw is designed to grip the pin 1 between its bearing face and the bottom of the groove 13. Gripping means equivalent to the screws 15 may be provided without departing from the scope of the invention.

Each sleeve 2 forms, at the opposite end of the jaw 11 and concentrically to the bore 9, an endpiece 16 which extends from a shoulder 17, the function of which will become obvious further on. The shoulder 17 ensures the connection between the endpiece 16 and a cylindrical bearing 18.

As illustrated in FIGS. 1 to 3, the endpiece 16, which is preferably cylindrical, of each connecting sleeve, is designed to receive and support the corresponding end portion of the arm of the tensioning stirrup 3. Said stirrup is constituted by two rigid arms 19 which are connected in their substantially median part, by means of pivot pins 20 to a rigid web 21. The homologous top (according to the drawing) end portions of the arms 19 comprise articulation means 22 such as pivot pins, in order to adapt the ends of a tension rod 23 which is, for example, constituted by a tapped sleeve 24 capable of cooperating simultaneously with two reversedly threaded rods 25.

The lower end portions of the arms 19 are provided with rings 26, for example mounted by means of pivot members 27. Each ring 26 defines a cylindrical housing 28 adapted to receive an endpiece 16, such housing being accessible through an axial hole 29 of diameter greater than the diameter of the pin 1, but smaller than that of the endpiece 16.

The cylindrical bearing 18 is designed to ensure the connection of each sleeve 2 with a corresponding bearing 4. Each bearing is constituted by a flange-like member 30 defining a bearing surface 31 adapted to receive the outer cage of a ball-bearing 23 whose inner cage is mounted on the cylindrical bearing 18. The flange-like member 30 is provided, in parallel to the axis of the bearing 31, with a hole 33 for hooking in the arms 34 of the stirrup 5. Preferably, according to the invention, the stirrup 5 is constituted by two half stirrups 5a and 5b each one comprising an arm 34a or 34b, one end of which is bent in 35a or 35b to cooperate with the hole 33, whereas the other end is looped over to form a closed hook 36a or 36b, both of which hooks are joined together by a closed ring.

The device according to the invention is used as follows:

First the pin 1 is made to go through the limb by being inserted into the bone thereof, according to the conventionally used methods. Each sleeve 2, structurally associated by the ball bearing 32 to the corresponding bearing 4, is threaded via the bore 9 on one end of the pin 1 on either side of the sick limb. The axial position of each sleeve 2 is determined by way of the clamp 10 whose jaw 14 is tightened on the pin 1 which is threaded through the said clamp on emerging from the bore 9 and after engagement into the groove 13. Said clamp 10 is tightened to prevent any risk of axial sliding with respect to the pin 1.

In this position, the stirrup 3 is astride the pin 1 by insertion into the grooves 29 of the rings 26 which are threaded on the endpieces 16 until they abut against the shoulders 17. There, the tension rod 23 can be operated via the sleeve 24, to control the relative opening movement in the direction of arrow $f_1$. The rings 26 are thus applied against the shoulders 17 and create a tension by traction of the pin 1.

It should be noted that the tensioning stirrup 3 can be assembled differently. For example, the stirrup may be positioned level with the pin 1 and the endpieces 16 of the sleeves 2 inserted in the housings 28, when adapting the sleeves on the end portions of the pin 1.

In this particular case, the device is completed by inserting the bent parts 35 of the half-hoops 5a and 5b into the flange-like pieces 30 which constitute the bearings 4. The half-hoops thus reconstitute the hoop 5 which can be connected to a suspension cable.

The reconstitution as indicated above of the device according to the invention is then completed, as illustrated in FIG. 4, by the angular immobilization of the stirrup 3 by means of a supporting member or bar 37 which is fixed, on the one hand, to the stirrup, and on the other hand and optionally, by a lug or a plate directly on the limb to be treated.

An examination of FIG. 1 shows that the device according to the invention dissociates the tensioning function of the pin 1 from the traction or suspension function of the hoop which is to suspend or to pull on said pin. Indeed, the sleeves 2 directly bear the strain of the axial traction imposed by the stirrup and which is reflected by the clamps 10 at the level of the ends of the pin 1.

The suspension function on the contrary is centered between the hoop 5 and the bearings 4 which are connected to the sleeves 2 via roller bearings 32. It should be noted that the latter are not subjected to any axial pressure from the stirrup 3, since the rings 26 rest against the abutting shoulders 17. The roller bearings 32 are therefore only acted upon in suspension, when they receive a radial pressure which does not prevent their free rotation since in this particular case, they work in the exact conditions in which they are normally meant to work.

In the example illustrated in FIG. 4, the leg to be reeducated is carried by a suspension splint fastened in two points to a structure, one of said points being joined to the hoop 5. Any movement in the direction of arrow $f_2$ or in the direction of arrow $f_3$, with a view to working the articulations, causes a rotation between the bearings 4 and the sleeves 2 which are not affected by such a movement, and therefore keep holding the pin 1 in the initial position without relative rotation inside the bone 7.

It should be noted that any interfering movement of rotation which could be due to friction is made impossible by the presence of the supporting member or bar 37 which keeps the stirrup in the initially selected angular position and even in relation to the mobilization of the limb.

FIG. 1 shows that each sleeve 2 comprises a supporting shoulder 39 for the roller bearing 32. Said shoulder 39 is formed close to the clamp 10, at the opposite end of endpiece 16. Consequently, after reconstituting the device and adapting it on a limb, the shoulders 39 are placed externally to members 30 of the bearings 4. Said shoulders 39, which are necessary for the assembly and initial adaptation, do not therefore transfer any axial stresses to the ball bearings.

Another advantage of the invention resides in the fact that the elements constituting the device eliminate all possibility of erroneous assembly when fitting and adapting it on the limb of a patient seeing that the endpieces must necessarily be threaded on the pin in facing relation so as to enable the assembly of the tensioning stirrup.

In addition, the different elements constituting the device are simple and solid and can, therefore, be used for long periods without requiring frequent and delicate maintenance.

Also the flange-like member 30 of the bearings 4 can be produced so that the device can be used directly on a suspended splint as illustrated in FIG. 4 or else on a resting-down splint. To this end, arrangement can be made for each member 30 to be provided with a hole 40, diametrically opposite the hole 33 and permitting the connection with a member 41 of a splint.

What is claimed is:

1. Traction-suspension device with transosseous pin, of the type comprising a pin designed to go through a bone and of which the end portions can be subjected to a traction, one with respect to the other, by means of an adjustable tension rod, wherein said device comprises:
    a tensioning pin and tension sleeves immobilizable in adjustable axial position on the pin,
    two support bearings receiving the said sleeves via ball bearings,
    a traction-suspension hoop adaptable on the bearings,
    a tensioning stirrup adaptable between the bearings on assembling endpieces formed by the sleeves in facing relation.

2. Device as claimed in claim 1, wherein each tension sleeve comprises a tubular endpiece which extends from an abutting shoulder connecting it to a cylindrical bearing provided for assembling the inner cage of a ball bearing connection with the corresponding bearing, the said sleeve being provided with an axial bore allowing the passage of the pin and issuing between the jaws of a clamp member formed by the sleeve on the opposite side of the endpiece.

3. Device as claimed in claim 2, wherein each sleeve is provided with an axial bore of greater diameter than the diameter of the pin, and wherein said jaws include a fixed jaw and a free jaw such that said bore issues on the level of the fixed jaw to comprise a groove in the fixed jaw, said groove extending from the axial bore and said groove having a radius equal to the radius of the pin and wherein said free jaw includes a supporting face which is adapted to clamp the pin against the fixed jaw.

4. Device as claimed in claim 2, wherein each sleeve is mounted by way of a roller bearing which is free to rotate in a supporting bearing formed by an elongated flange-like member comprising in at least one of its end-portions, a hole for hooking in one of the arms of the hoop.

5. Device as claimed in claim 4 wherein each sleeve is mounted in a flange-like member comprising a hole for its adaptation on to a supporting and/or mobilization splint.

6. Device as claimed in claim 1, wherein the traction-suspension hoop is constituted by two half-hoops.

7. Device as claimed in claim 1, wherein each tension sleeve comprises a tubular endpiece which extends from an abutting shoulder and wherein the tensioning stirrup comprises two arms mounted for pivoting by their substantially median part on a rigid web and comprising, at the level of their homologous ends, on the one hand, means connecting them with a tension rod means of adjustable length and on the other hand, axially split rings adapted to be threaded on the endpieces of the sleeves until they rest against the abutting shoulders.

8. Device as claimed in claim 1, further comprising a supporting member means fixed to the stirrup so that the pin will be prevented from rotating relative to the bone.

* * * * *